United States Patent [19]

Knollenberg

[11] Patent Number: 4,636,075
[45] Date of Patent: Jan. 13, 1987

[54] PARTICLE MEASUREMENT UTILIZING ORTHOGONALLY POLARIZED COMPONENTS OF A LASER BEAM

[75] Inventor: Robert G. Knollenberg, Boulder, Colo.

[73] Assignee: Particle Measuring Systems, Inc., Boulder, Colo.

[21] Appl. No.: 643,665

[22] Filed: Aug. 22, 1984

[51] Int. Cl.$^4$ ............................................. G01N 15/14
[52] U.S. Cl. .................................... 356/336; 356/338
[58] Field of Search ................................ 356/336, 338

[56] References Cited

U.S. PATENT DOCUMENTS

| | | |
|---|---|---|
| 3,406,289 | 10/1968 | Schleusener. |
| 4,188,122 | 2/1980 | Massie et al. .................. 356/360 X |
| 4,272,193 | 6/1981 | Eastman et al. . |
| 4,284,355 | 8/1981 | Hansen et al. . |
| 4,329,054 | 5/1982 | Bachalo ............................. 356/336 |
| 4,348,111 | 9/1982 | Goulas et al. .................... 356/338 X |
| 4,387,993 | 6/1983 | Adrian .............................. 356/336 |
| 4,444,500 | 4/1984 | Flinsenberg et al. ............. 356/336 |

Primary Examiner—Davis L. Willis
Assistant Examiner—Matthew W. Koren
Attorney, Agent, or Firm—Robert E. Harris

[57] ABSTRACT

Particle measurement is disclosed utilizing orthogonally polarized components of a laser beam. A laser beam is split into orthogonally polarized components and at least one of the components is thereafter beam shaped to have a modified dimension. The components are then recombined and focused to provide a beam combination that is directed through a particle containing volume where scattering of the components occurs by the particles. With the components superimposed upon one another, a localized volume is created with one beam being contracted to a smaller volume than the other beam with the illumination intensity ratios thereat being either greater or less than unity depending upon the optics selected. Particle scattering events are observed within the localized volume in order to define those particles transitting through its central uniform intensity region (sample volume) independent of viewing circumstance by comparing scattered intensity ratios of the orthogonally polarized beam components using a polarizing analyzer and a pair of detectors. The scattering intensities measured of those particles transitting through the preferred sample volume are retained as valid size measurements. With the components in juxtaposition with respect to one another, flow velocity measurement is enabled by measurement of the transit times between the juxtapositioned components.

26 Claims, 6 Drawing Figures

PARTICLE MEASUREMENT UTILIZING ORTHOGONALLY POLARIZED COMPONENTS OF A LASER BEAM

FIELD OF THE INVENTION

This invention relates to particle measurement by use of a laser beam and, more particularly, relates to such measurement utilizing orthogonally polarized components of a laser beam.

BACKGROUND OF THE INVENTION

It is oftentimes desired that the size and/or velocity of small particles be measured and devices have been heretofore suggested and/or utilized to accomplish this end. It has been heretofore found, for example, that small particles can be measured by directing the particles through a laser beam and determining particle size by collecting light scattered by the beam (see, for example, U.S. Pat. No. 3,406,289).

While such measurements have been found to be useful for detecting particle size, such systems have generally heretofore required that the particles be directed through the center of the laser beam where the intensity is the greatest and can be considered to be uniform.

It has also been heretofore suggested that a laser beam could be split and the resulting beams thereafter utilized, and such split beams have been used heretofore, for example, to compare optical path lengths in a multiple laser beam fusion system (see U.S. Pat. No. 4,272,193). In addition, laser beams have heretofore been combined and the combined beam utilized to evaluate cell volume, for example, by providing fluorescence volume exclusion signals (see U.S. Pat. No. 4,284,355).

SUMMARY OF THE INVENTION

This invention provides a particle measurement device and method wherein a pair of orthogonally polarized components of a laser beam are combined, after being separately processed to modify a dimension of at least one of the components, to form a beam combination that is directed through a particle containing sample volume where component scattering occurs by the particles, without neccessity that the particles be at the center of the beam, with the scattered components being thereafter collected and a reliable determination of particle measurement made therefrom.

It is therefore an object of this invention to provide an improved system and method for particle measurement using a laser beam.

It is another object of this invention to provide a system and method for particle measurement using orthogonally polarized components of a laser beam.

It is another object of this invention to provide a system and method for particle measurement using orthogonally polarized components that have been separately processed to modify at least one of the components and then combined prior to being directed toward particles to be measured.

It is still another object of this invention to provide a system and method for particle measurement using a laser beam wherein the particles to be measured need not pass through the center of the beam to accomplish measurement.

It is still another object of this invention to provide a system and method for particle size measurement using orthogonally polarized components of a laser beam.

It is still another object of this invention to provide a system and method for particle velocity measurement using orthogonally polarized components of a laser beam.

It is yet another object of this invention to provide a system and method for particle measurement using orthogonally polarized components of a laser beam wherein one component is used to accomplish measurement and the other is used to verify the acceptability of such measurement.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which.

DESCRIPTION OF THE INVENTION

In this invention, a polarized laser beam is first split into orthogonally polarized components, and at least one component (or both if desired) is then independently beam shaped, after which the beam components are recombined to form a beam combination with one of the components having a modified dimension relative to the other component. The beam combination is then focused to create a localized volume where one beam contracts to a smaller dimension than the other beam.

With the components of the beam combination superimposed with respect to one another, a sample volume is defined wherein the illumination intensity ratios are either greater or less than unity depending upon the optics selected. Observation of particle events near this sample volume allows defining of particle position, relative to the sample volume, independent of viewing circumstance simply by comparing scattered intensity ratios of the orthogonally polarized components using a polarizing analyzer and a pair of detectors.

With the components of the beam combination in juxtaposition with respect to one another, measurement of transit time between the juxtapositioned components affords flow velocity measurement.

Through use of this invention, a localized region of interest can be defined within a light beam. This enables particle size measurements to be made with a laser light source without the necessity for injecting a microstream of particles through the center of the laser beam (the intensity is the greatest and can be considered uniform at the center of a laser beam). In essence, this is accomplished by observing particles transitting through the field-of-view of the observing optical system, and based upon localized trojectories, making a decision to accept or reject size measurements performed.

Figure 1:
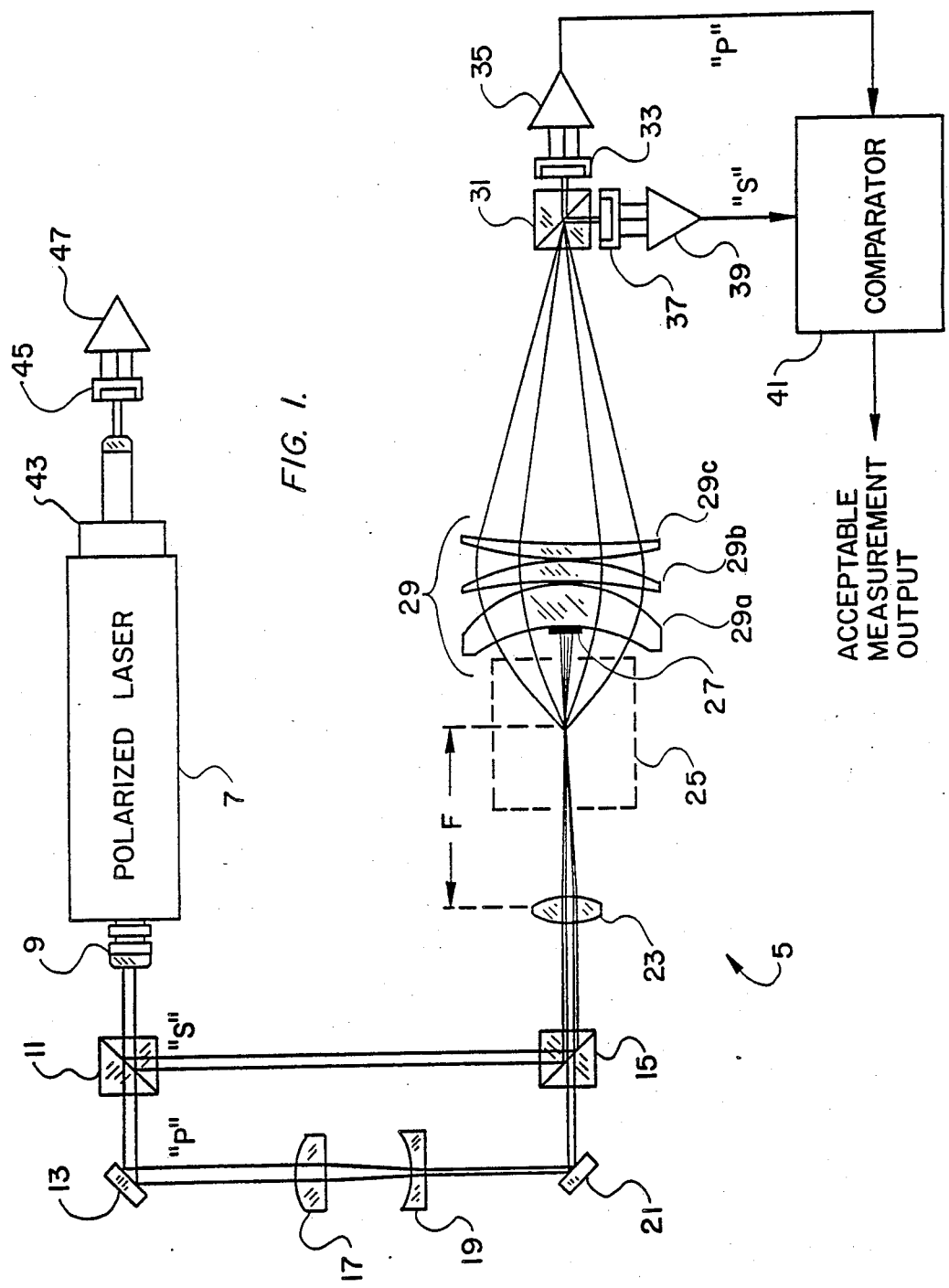
FIG. 1 is an optical diagram illustrating the invention.

Referring now to FIG. 1, the system 5 of this invention is shown to include a polarized laser 7 as a light source. The frequency or power level of the laser is not critical and can be any frequency and/or power level known in the field of particle measurement. In addition, laser 7 can be either multi-mode or fundamental-mode (TEMoo) and, while polarization is preferred, it is not required so long as the laser beam has at least one stable polarization state (the simplest way to assure this being, for example, to plane polarize the laser with an internal Brewster's window).

Laser 7 has an output mirror 9 at one end through which the polarized beam is discharged from the laser toward polarizing beamsplitter cube 11. At beamsplitter cube 11, the plane of polarization of the laser is oriented at 45° to the diagonal interface of polarizing beamsplitter cube 11 which results in the light being split into two equal orthogonally polarized components "S" and "P" (the reflected beam is herein designated as "S" and the transmitted beam is designated herein as "P").

As shown by way of example in FIG. 1, the two beam components are treated independently. The "P" component beam is coupled to mirror 13 (after which the beam undergoes beam shaping as brought out hereinafter), while the "S" component beam remains collimated and is coupled to polarizing beamsplitter cube 15. In the example shown in FIG. 1, beam shaping of the "P" component consists of contracting the beam in one dimension using positive and negative cylindrical lenses 17 and 19 positioned so that the emerging beam is elliptical, although essentially recollimated. This modified beam (i.e., having one dimension modified) is then directed to mirror 21 which directs the beam to polarizing beamsplitter cube 15.

Figure 2A:
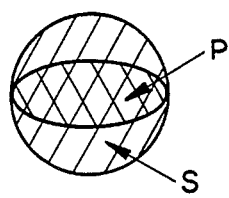
FIG. 2(a) is an illustration of typical superimposed beams of a beam combination after recombining of the separately processed beam components in the device as shown in FIG. 1.
Figure 2B:
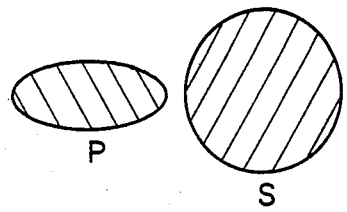
FIG. 2(b) is an illustration of typical juxtapositioned beams of a beam combination after recombining of the separately processed beams in the device shown in FIG. 1.

At beamsplitter cube 15, the "S" and "P" beam components are recombined to form a beam combination. Emerging from beamsplitter cube 15, the beam combination of the "S" and "P" beam components may be either superimposed (as shown in FIG. 2(a)) or juxtaposed (as shown in FIG. 2(b)) with respect to one another. In either event, the beams have equal widths in one dimension while the "P" component beam has been contracted in the opposite dimension.

Figure 3A:
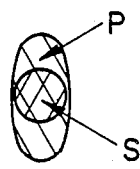
FIG. 3(a) is an illustration of a superimposed beam combination, as shown in FIG. 2(a), after focusing.
Figure 3B:
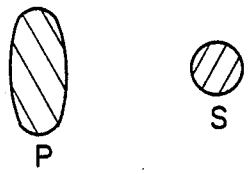
FIG. 3(b) is an illustration of a juxtaposed beam combination, as shown in FIG. 2(b), after focusing.

Condensing lens 23 is then used to focus the beam combination into a region of viewing interest (designated as sample viewing region 25 in FIG. 1). At the focus of condensing lens 23, the ellipticity of the "P" beam effectively inverts (as shown in FIG. 3(a)). As indicated by a comparison of FIGS. 2(a) and 3(a), the "P" polarized beam is now elongated in the dimension in which it was previously foreshortened.

Figure 4:
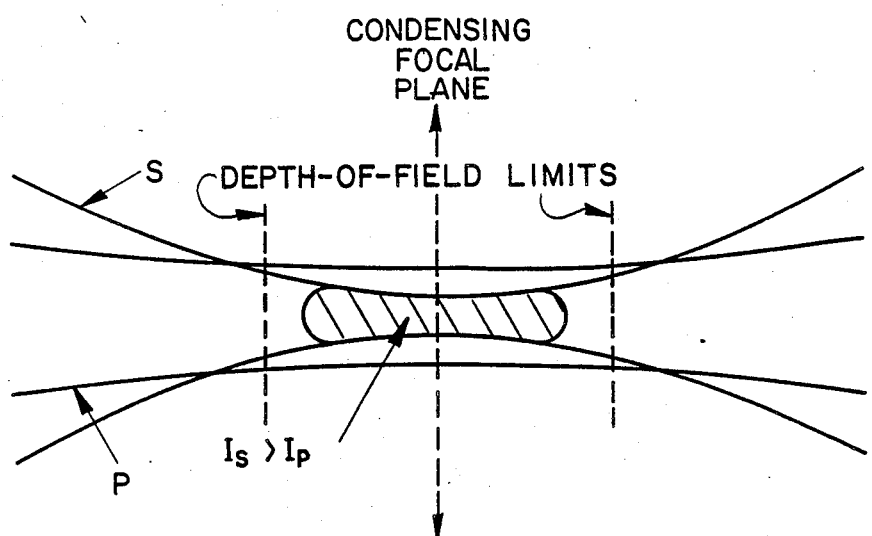
FIG. 4 is an illustration of typical differences in component convergence near focus for the beam combination shown in FIG. 3(a), with intensity variations also being illustrated.

As shown in FIG. 4, at the region (localized volume) near the focus of the condensing lens, the "S" polarized component converges more rapidly than does the "P" polarized component. Assuming that the beams were of equal power, a central uniform intensity region (sample volume) is defined where the "S" polarized component intensity is equal to or greater than the "P" component intensity.

When a particle passes through this beam pair, or combination, both the "S" and "P" components are scattered. The transmitted light (not scattered) is collected and absorbed by light trap (dump spot) 27 centrally positioned at the front central portion of collecting optics 29. The scattered light falling outside light trap 27 is separated from the transmitted light by using a set of collecting optics 29 (such as lenses 29a, 29b and 29c coaxially positioned as indicated in FIG. 1, although it is to be realized that the optics could be arranged at a variety of angles).

The scattered light collected within the clear aperture outside the light trap (at collecting optics 29) is reimaged by collecting the scattered light at collecting polarizing beamsplitter cube 31 where the polarized components are separated with the "P" component being coupled to detector 33 connected with "P" photodiode preamplifier 35 and with the "S" component being coupled to detector 37 connected with "S" photodiode preamplifier 39. Detectors 33 and 37 thus view reconstructed light particle images within a dark field of the complementary "S" and "P" polarized states with the aid of polarizing beamsplitter cube 31.

By comparing, at comparator 41, the signal amplitudes of the "S" and "P" components generated by particles passing through the sample area, the following observations can be made: whenever the measured intensity for the "S" scattering component is equal to or greater than the "P" scattering component, the particle trajectory must have intercepted the central region (as shown in FIG. 4); and whenever the "S" scattering signal is less than the "P" scattering signal, the particle trajectory must have intercepted regions outside the central sample volume (regions where the "S" component is greater than the "P" component at large distances from the center of the sample volume as depicted in FIG. 4 need not be considered because they are beyond the depth-of-field limits of the collecting optics).

In cases where the beam pair is juxtaposed rather than superimposed, the particle flow must be aligned in the direction of the diplaced beams of the beam combination such that the trajectories result in a similar set of scattering amplitudes even though the pulse pair is separated in time. Using a known displacement, particle velocity measurement can be made by simply measuring the time between the pulse pair.

Utilized in the manner above set forth, the "P" component beam is utilized for particle size measurements of the central uniform intensity region, while the "S" component simply establishes a region of localized interest within the "P" component beam. In practice, the "P" component beam is designated as the "measurement" beam, while the "S" component beam is designated as the "acceptance" beam. In other words, as long as the "S" polarized component is equal to or greater than the "P" polarized component in scattering intensity, the measurement of particle size afforded by the "P" beam component is accepted. If such is not the case, then the measurement is rejected.

As also indicated in FIG. 1, laser 7 can also optionally provide a reference output through output mirror 43 to reference photodiode 45 connected with photodiode preamplifier 47 of a reference photodetector module.

In a working emodiment of this invention, good noise immunity has been achieved by the necessary correlation of the two independent measurements. Optical system complexity has also been reduced by using simple condensing optics instead of complex collecting imaging optics (the collecting optics can also be arranged in almost any orientation so long as the optics refocus the scattered light within the detector apparatus), and it has been found that it is not necessary that the apparatus reconstruct accurate, detailed particle images, with the requirement for exact alignment also being mitigated.

As can be appreciated from the foregoing, this invention provides an improved device and method for particle measurement utilizing orthogonally polarized components of a laser beam.

What is claimed is:

1. A particle measuring system, comprising:
   beam generating means for generating first and second beams that are orthogonally related to one another;
   processing means for receiving said first beam from said beam generating means and modifying one dimension of said first beam relative to the other dimension thereof;
   combining means for combining said modified first beam and said second beam to provide a beam combination output;
   exposure means for receiving said beam combination output from said combining means and exposing said beam combination to particles to be measured so that portions of said beam combination are scattered by said particles; and
   determining means for collecting at least some of said scattered portions of said beam combination and providing therefrom an output indicative of the measurement of said particles.

2. The system of claim 1 wherein said beam generating means includes a laser providing an output beam and beam-splitting means receiving said output from said laser and generating therefrom said first and second orthogonally related beams.

3. The system of claim 2 wherein said laser provides a polarized output beam, and wherein said beamsplitting means is a polarizing beamsplitter cube having a diagonal interface receiving said polarized beam output from said laser at a 45° angle with respect to said diagonal interface.

4. The system of claim 1 wherein said processing means includes lens means to modify said first beam by contracting one dimension thereof relative to the other dimension thereof.

5. The system of claim 1 wherein said combining means includes a polarizing beamsplitter cube for separately receiving said modified first beam and said second beam.

6. The system of claim 1 wherein said determining means includes collecting means for collecting said scattered portions of said beam combination, splitting means for receiving said collected scattered portions of said combination beam output and splitting the same into a first path if said scattered portions originated from said first beam and into a second path if said scattered portions originated from said second beam, and detecting means receiving said scattered portions from each said path to determine therefrom said particle measurement.

7. The system of claim 6 wherein said collecting means includes a collecting optics lens assembly for receiving said scattered portions of said beam combination and a light trap for receiving nonscattered portions of said beam combination.

8. The system of claim 6 wherein said splitting means includes a collecting polarizing beamsplitting cube.

9. The system of claim 6 wherein said detecting means includes a first detector for receiving said scattered portions of said beam combination originating from said first beam, and a second detector for receiving said scattered portions of said beam combination originating from said second beam, and wherein said system includes comparator means for comparing said outputs from said detectors.

10. A particle measuring system, comprising:
    laser means providing a laser beam output;
    beamsplitting means for receiving said laser beam output and providing a "P" component and an "S" component with said "P" component being orthogonally related to said "S" component;
    beam modifying means for modifying said "P" component in one dimension relative to the other dimension thereof;
    combining means for receiving said modified "P" component and said "S" component and recombining said components to provide a beam combination;
    focusing means for focusing said beam combination within a volume capable of having particles therein to be measured;
    collecting means for receiving portions of said beam combination scattered by particles within said volume;
    polarizing analyzer means for receiving said scattered portions of said beam combination collected by said collecting means and separating the same into "P" components and "S" components; and
    detector means connected to receive each of said scattered "P" components and "S" components from said polarizing analyzer means and providing therefrom signals indicative of measurement of particles within said volume.

11. The system of claim 10 wherein said system includes comparator means connected with said detector means for comparing said signals indicative of said scattered "P" components and said scattered "S" components and providing therefrom and indication of particle measurement that has been tested for acceptance.

12. The system of claim 11 wherein said focusing means causes said "S" components to converge more rapidly than said "P" components to provide different intensity areas within said volume, and wherein said comparator means compares scattered intensity ratios of said "P" and "S" components to define a preferred sample volume.

13. The system of claim 12 wherein said "P" components provide an indication of particle measurement and said "S" components provide an indication of the acceptability of said particle measurement made from said "P" components.

14. The system of claim 10 wherein said combining means provides said beam combination with said "P" and "S" components being superimposed upon one another, and wherein said detector means provides an output indicative of size measurement.

15. The system of claim 10 wherein said combining means provides said beam combination with said "P"

and "S" components being in juxtaposition with respect to one another, and wherein said detector means provides an output indicative of velocity measurement.

16. The system of claim 10 wherein said scattered portions of said beam combination received at said polarizing analyzer means are reimaged thereat, and wherein said detector means view reconstructed bright particle images within a dark field of complementary "P" and "S" polarized states.

17. A method for measuring particles, said method comprising:
generating first and second beams that are orthogonally related to one another;
modifying one dimension of said first beam relative to the other dimension thereof;
combining said modified first beam with said second beam to provide a beam combination output;
directing said beam combination toward particles to be measured so that portions of the beam combination are scattered thereby;
separating the scattered portions of said beam combination into different groups depending upon beam origination; and
utilizing the separate groups to determine particle measurement.

18. The method of claim 17 wherein said beam generation includes generating a polarized laser beam and splitting "S" and "P" components thereof into orthogonally related beam components.

19. The method of claim 18 wherein said separating of "S" and "P" components includes receiving a polarized laser beam at a 45° angle with respect to the diagonal interface of a beamsplitting cube.

20. The method of claim 17 wherein said modification of said first beam includes contracting one dimension of said beam with respect to the other dimension of said beam.

21. The method of claim 17 wherein said combining of said beams includes superimposing said beams upon one another with one beam converging faster than the other and having a greater intensity at a sample volume to thereby enable reliable particle measurement.

22. The method of claim 21 wherein said determination of particle measurement includes providing electrical signals with respect to each of said first and second beams the amplitude of each of which depends upon the positioning of particles scattering the beams relative to said sample volume to thereby provide both a measurement of particles and the acceptability of measurement.

23. The method of claim 17 wherein said combining of said beams includes providing said beams in juxtaposition with respect to one another to enable particle velocity measurement.

24. A method for measuring particles, said method comprising:
generating a polarized laser beam;
providing a beamsplitter having a diagonal interface to receive the generated polarized laser beam at a 45° angle so that orthogonally related "S" and "P" beam components are provided;
modifying one dimension of said "P" component relative to the other dimension thereof;
combining said modified "P" component with said "S" component to form a beam combination;
focusing said beam combination within a volume where particles to be measured are illuminated so that the "S" component converges more rapidly than does the "P" component with said "S" component having greater intensity at at least one predetermined segment to thus define a sample volume;
causing said beam combination to illuminate particles within said sample area so that said beam combination is scattered;
collecting said scattered segments of said beam combination;
splitting said scattered segments into a first group containing scattered "P" components and a second group containing scattered "S" components;
providing first and second electrical signals having an amplitude dependent upon the scattered intensity ratios of said "P" and "S" components in said first and second groups; and
comparing said electrical signals to determine size measurement of said particles from said "P" component and acceptability of said size measurement from said "S" component.

25. The method of claim 24 wherein said "P" component is modified by contracting one dimension thereof relative to the other dimension, and wherein said modified "P" component and said "S" component are combined by being superimposed upon one another.

26. The method of claim 24 wherein said scattered segments of said beam combination are reimaged, and wherein said first and second electrical signals are formed by detectors viewing reconstructed bright particle images within a dark field of complementary "P" and "S" polarized states.

* * * * *